(12) United States Patent
Løjkner et al.

(10) Patent No.: US 11,692,994 B2
(45) Date of Patent: Jul. 4, 2023

(54) SEAL ENHANCER

(71) Applicant: SOPHION BIOSCIENCE A/S, Ballerup (DK)

(72) Inventors: Lars Damgaard Løjkner, Copenhagen (DK); Anders Lindqvist, Lund (SE); Daniel Rafael Sauter, Copenhagen (DK); Kadla Røskva Rosholm, Copenhagen (DK)

(73) Assignee: SOPHION BIOSCIENCE A/S, Ballerup (DK)

( * ) Notice: Subject to any disclaimer, the term of this patent is extended or adjusted under 35 U.S.C. 154(b) by 0 days.

(21) Appl. No.: 17/514,427

(22) Filed: Oct. 29, 2021

(65) Prior Publication Data

US 2022/0107304 A1 Apr. 7, 2022

Related U.S. Application Data

(63) Continuation of application No. 16/465,590, filed as application No. PCT/EP2017/081388 on Dec. 4, 2017, now Pat. No. 11,215,606.

(60) Provisional application No. 62/449,278, filed on Jan. 23, 2017.

(30) Foreign Application Priority Data

Dec. 2, 2016 (DK) .......................... PA 2016 70957

(51) Int. Cl.
*G01N 33/487* (2006.01)
*A61P 1/00* (2006.01)
*C07K 1/00* (2006.01)

(52) U.S. Cl.
CPC .............. *G01N 33/48728* (2013.01)

(58) Field of Classification Search
CPC .... A61P 1/00; C07K 1/00; C12N 1/00; G01N 1/00; G01N 2201/00; C12Q 1/00; C12Q 2304/00
See application file for complete search history.

(56) References Cited

U.S. PATENT DOCUMENTS

| | | | | |
|---|---|---|---|---|
| 6,126,801 | A | * 10/2000 | Sokalski | ............ G01N 27/3335 204/418 |
| 2003/0149129 | A1 | * 8/2003 | Dickens | ................... C08K 3/32 523/116 |
| 2004/0168912 | A1 | 9/2004 | Klemic et al. | |

(Continued)

FOREIGN PATENT DOCUMENTS

| | | |
|---|---|---|
| EP | 1042468 A2 | 10/2000 |
| EP | 1775586 A1 | 4/2007 |

(Continued)

OTHER PUBLICATIONS

International Application No. PCT/EP2017/081388, International Search Report and Written Opinion, dated Feb. 16, 2018.

(Continued)

*Primary Examiner* — Jermele M Hollington
*Assistant Examiner* — Temilade S Rhodes-Vivour
(74) *Attorney, Agent, or Firm* — Marshall, Gerstein & Borun LLP

(57) ABSTRACT

A seal enhancer for improving the patch clamp seal in a patch clamp method or apparatus is provided. The internal solution comprises particular anions and the external solution comprises one or more metal ions at low concentration.

20 Claims, 1 Drawing Sheet

(56) References Cited

U.S. PATENT DOCUMENTS

| | | | |
|---|---|---|---|
| 2007/0087327 A1 | 4/2007 | Fertig et al. | |
| 2009/0098546 A1 | 4/2009 | Penner et al. | |
| 2010/0087446 A1 | 4/2010 | Chakravarty et al. | |
| 2010/0259286 A1* | 10/2010 | Prodan | G01N 33/6872 506/10 |
| 2011/0014642 A1 | 1/2011 | Barhanin et al. | |
| 2011/0166136 A1 | 7/2011 | Khan et al. | |
| 2012/0190583 A1* | 7/2012 | Gillis | C12N 13/00 506/10 |
| 2013/0147461 A1* | 6/2013 | Schmidt | G01N 33/48728 422/502 |
| 2014/0339102 A1 | 11/2014 | Urisu et al. | |
| 2016/0209395 A1* | 7/2016 | Urisu | G01N 33/48728 |
| 2017/0256802 A1 | 9/2017 | Mosby et al. | |

FOREIGN PATENT DOCUMENTS

| | | |
|---|---|---|
| JP | H10509794 A | 9/1998 |
| JP | 2005520540 A | 7/2005 |
| JP | 2011-501657 A | 1/2011 |
| JP | 2016-510210 A | 4/2016 |
| JP | 2016-518853 A | 6/2016 |
| WO | WO-1996/13721 A1 | 5/1996 |
| WO | WO-2003/080570 A2 | 10/2003 |
| WO | WO-2014/095875 A1 | 6/2014 |
| WO | WO-2014/186793 A2 | 11/2014 |

OTHER PUBLICATIONS

Obergrussberger et al., Automated Patch Clamp Meets High-Throughput Screening: 384 Cells Recorded in Parallel on a Planar Patch Clamp Mode, *J. Lab. Auto.*, 21(6):779-793 (2016).

Priel et al., Ionic Requirements for Membrane-Glass Adhesion and Giga Seal Formation in Patch-Clamp Recording, *Biophysical Journal*, 92: 3893-3900 (2007).

* cited by examiner

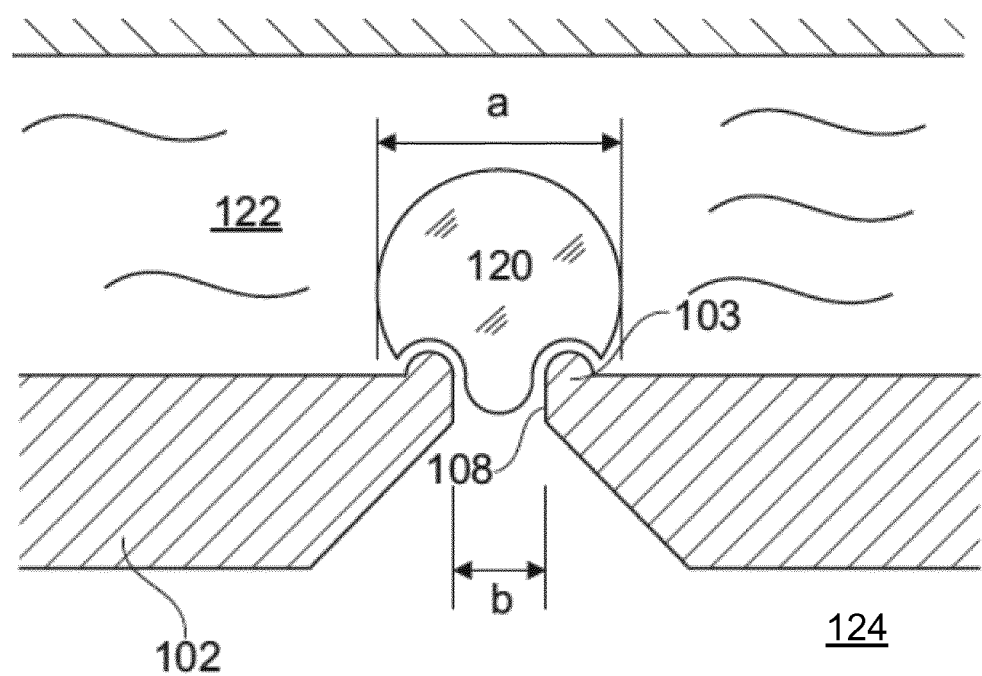

SEAL ENHANCER

TECHNICAL FIELD

A seal enhancer for improving the patch clamp seal in a patch clamp method or apparatus is provided.

BACKGROUND

A critical step in a planar patch clamp experiment is the seal formation i.e. formation of a tight bond between the cell membrane and the substrate of the planar patch clamp chip. This seal poses a barrier for charge carriers such as ions and a good seal can therefore be measured as a high seal resistance. The exact mechanism by which this connection occurs remains to be completely understood, however, it is known that small gaps between the cell and the substrate can be closed (sealed) by precipitation of a salt. To exploit this effect, it is important to have both components of this salt (i.e. anions and cations) separated in internal and external solution; otherwise, the salt would already start to precipitate before the cell is applied and this would result in an altered ionic strength of the solution. Solubility of a solution is defined in the solubility product $K_{sp}$. The smaller $K_{sp}$, the fewer ions are freely available and the more are present as solid salt. $R_{membrane}$ was historically enhanced using fluoride in the internal solution and $Ca^{2+}$ in the external. $CaF_2$ has a $K_{sp}$ of $3.58 \times 10^{-11}$ (McCann, 1968), thus $CaF_2$ precipitates at the interface between internal and external solution thus fostering seal formation (Vargas, Yeh, Blumenthal, & Lucero, 1999). However, there are certain applications that require $Ca^{2+}$ in the internal solution and in the external solution (e.g. $Ca^{2+}$-activated $K^+$ and $Cl^-$ channels) and the use of F— in these solutions is not feasible due to the low $K_{sp}$.

Typically, the concentration of metal ions in the external solution is in the region of 50-100 mM, cf. EP1775586. However, too metal ion concentrations may possibly affect ion channel function in an adverse manner leading to incorrect responses and inaccuracies in drug target responses.

There is a need for a seal enhancer for a patch clamp system, which is compatible with other components of internal or external solutions. In certain circumstances the content of F ions is reduced or even eliminated.

SUMMARY

A patch clamp system is provided. The patch clamp system comprised a patch clamp device, an internal solution and an external solution. The internal solution comprises one or more anions selected from phosphate ($PO_4^{3-}$) ions, sulfate ($SO_4^{2-}$) ions and fluoride ($F^-$) ions, and the external solution comprises one or more metal ions selected from $Ca^{2+}$, $Sr^{2+}$ and $Ba^{2+}$, or combinations thereof. The concentration of said metal ions in the external solution is between 1 and 20 mmol/L.

The use of one or more anions selected from phosphate ($PO_4^{3-}$), sulfate ($SO_4^{2-}$) and fluoride ($F^-$) anions in combination with one or more metal ions selected from $Ca^{2+}$, $Sr^{2+}$ and $Ba^{2+}$, or combinations thereof as a seal enhancer in a patch clamp system is also provided, wherein the anions are present in an internal solution, and the metal ions are present in an external solution of the patch clamp system. The concentration of said metal ions in the external solution is between 1 and 20 mmol/L A method for providing a gigaseal in a patch clamp system is also provided, in which the patch clamp system comprises a patch clamp device, an internal solution and an external solution. The method comprising the steps of:
 a. introducing a solution of one or more anions selected from phosphate ($PO_4^{3-}$), sulfate ($SO_4^{2-}$) and fluoride ($F^-$) anions into the internal solution;
 b. introducing a solution of cells into the external solution, and capturing the cells within the patch clamp device;
 c. introducing a solution of one or more metal ions selected from $Ca^{2+}$, $Sr^{2+}$ and $Ba^{2+}$ or combinations thereof into the external solution, wherein the concentration of said metal ions in the external solution is between 1 and 20 mmol/L
wherein steps a and b. can be performed in any order.

FIGURE

FIG. 1 shows a simplified view of a patch clamp device 102 for use in patch clamp analysis of a cell 120 sealed to the chip 102 to form a gigaseal. The device 102 separates an external solution 122 on a first side of the device from an internal solution 124 on an opposite side thereof. The diameter a of the cell is approximately 5-20 μm, such as approximately 10 μm. A hole 108 is formed in the device 102, through which suction may be applied to secure the cell 120 in place over the hole 108. Electrodes (not shown) may be provided in both sides of the device in order to determine an electrical resistance, a flow of ions or a voltage difference across the cell and through the hole 108.

DETAILED DISCLOSURE

Herein, the expression "external solution" refers to "extracellular physiological solution", external meaning outside the cell.

The expression "internal solution" refers to "intracellular physiological solution", internal meaning inside the cell or the solution intended to provide electrical and fluidic contact with the inside of the cell.

In a first aspect, a patch clamp system is provided, as illustrated schematically in FIG. 1. The patch clamp system comprises a patch clamp device 102, an internal solution 124 and an external solution 122.

The patch clamp system may be useful for determining or monitoring current flow through ion channel-containing structures such as cell membranes, with a high throughput and reliability and under conditions that are realistic with respect to the influences to which the cells or cell membranes are subjected. Thus, the results determined, e.g., variations in ion channel activity as a result of influencing the cell membrane with, e.g., various test compounds, can be relied upon as true manifestations of the proper influences and not of artefacts introduced by the measuring system, and can be used as a valid basis for studying electrophysiological phenomena related to the conductivity or capacitance of cell membranes under given conditions.

The current through one or more ion channels is directly measured using reversible electrodes as characterized below, typically silver/silver halide electrodes such as silver chloride electrodes, as both measuring electrodes and reference electrodes.

The patch clamp device may comprise an array of a plurality of chips on a single carrier. It may be is used in a method for determining and/or monitoring electrophysiological properties of ion channels in ion channel-containing structures, typically lipid membrane-containing structures such as cells, by establishing an electrophysiological measuring configuration in which a cell membrane forms a high resistive seal around a measuring electrode, making it possible to determine and monitor a current flow through the cell membrane. The patch clamp system is for example useful in a method for analysing the electrophysiological properties of a cell membrane comprising a glycocalyx. The patch clamp system may be used in or form part of an apparatus for studying electrical events in cell membranes, such as an apparatus for carrying out patch clamp techniques utilised to study ion transfer channels in biological membranes.

The internal solution comprises one or more anions selected from phosphate ($PO_4^{3-}$), sulfate ($SO_4^{2-}$) and fluoride ($F^-$) anions, preferably sulfate ($SO_4^{2-}$) ions. The concentration of anions, such as sulfate ($SO_4^{2-}$) ions, in the internal solution is between 20 and 200 mmol/L, suitably between 45 and 175 mmol/L, more suitably between 50 and 150 mmol/L, even more suitably between 75 and 125 mmol/L, inclusive, most suitably around 100 mmol/L.

To the best of our knowledge, $SO_4^{2-}$ does not inhibit any ion channel or relevant up-stream pathway.

Most sulfate salts are highly soluble in water, under physiological conditions. This allows a relatively broad spectrum of anions to be incorporated in the internal solution. Typically, sulfate ions are provided in the internal solution in the form of $Mg^{2+}$, $Ca^{2+}$, $K^+$ or $Na^+$ salts, preferably $K^+$ or $Na^+$ salts.

In order that sulfate salts do not precipitate in the internal solution before precipitation is required, the internal solution is suitably substantially free from ions which may cause sulfate precipitation. The internal solution is preferably substantially free from $Ba^{2+}$, $Fe^{3+}$ or $Be^2$ ions, and is preferably completely free from $Ba^{2+}$, $Fe^{3+}$ or $Be^e$ ions.

The external solution comprises one or more metal ions selected from $Ca^{2+}$, $Sr^{2+}$ and $Ba^{2+}$, or combinations thereof. Suitably, the metal ions are $Ba^{2+}$.

The concentration of the metal ions in the external solution is between 1 and 20 mmol/L, suitably between 4 and 17 mmol/L, more suitably between 5 and 15 mmol/L, even more suitably between 7.5 and 12.5 mmol/L, inclusive, most suitably around 10 mmol/L. $Ba^{2+}$ is known to inhibit some $K^+$ channels in the μM to low mM-range (Wulff & Zhorov, 2008). However, to the best of our knowledge, $Ba^{2+}$ does not have any effect on any of the $Cl^-$ channels. Once the seal is formed, the high $Ba^{2+}$ solution can be washed out again and the high seal will last for some more time. Therefore, the here described seal enhancer will also be useful for patch clamp applications where $Ba^{2+}$ functions as an inhibitor (e.g. inward rectifier $K^+$ channels).

In order that metal salts do not precipitate in the external solution before precipitation is required, the external solution is suitably substantially free of ions which may cause metal ion precipitation. The external solution is preferably substantially free from sulfate, and is preferably completely free from sulfate ions. The one or more metal ions are suitably added in the form of their $Cl^-$ salt. Suitably, all cations in the external solution are $Cl^-$.

In particular, the internal solution may have a concentration of fluoride ($F^-$) ions which is less than 5 mmol/L, suitably less than 1 mmol/L, and is more preferably zero. Fluoride ions can therefore be reduced and/or eliminated.

Without being bound by theory, it is hypothesised that— in the patch clamp system and method described herein— salts such as $BaSO_4$ precipitate at the interface between internal and external solution, thereby closing any gap between cell and patch hole.

$BaSO_4$ has a solubility constant of $K_{sp}=1.1×10-10$, and most importantly the Ksp of $CaSO_4$ is $4.93×10^{-5}$ meaning that $CaSO_4$ has a much lower tendency to precipitate from the internal solution if $SO_4^{2-}$ is added in the presence of $Ca^{2+}$. Therefore the internal solution and/or the external solution may additionally comprise calcium ($Ca^{2+}$) ions.

In a second aspect, the use of one or more anions selected from phosphate ($PO_4^{3-}$), sulfate ($SO_4^{2-}$) and fluoride ($F^-$) anions in combination with one or more metal ions selected from $Ca^{2+}$, $Sr^{2+}$ and $Ba^{2+}$, or combinations thereof as a seal enhancer in a patch clamp system is provided. In particular, the use of sulfate ($SO_4^{2-}$) ions in combination with metal ion selected from $Ba^{2+}$ as a seal enhancer in a patch clamp system is provided. The anions are present in an internal solution, and the metal ions are present in an external solution of the patch clamp system. In a similar manner to above, the concentration of said metal ions in the external solution is between 1 and 20 mmol/L.

All details of the first aspect, above, are also relevant to this second aspect.

In a third aspect, a method for providing a gigaseal in a patch clamp system is provided, in which the patch clamp system comprises a patch clamp device, an internal solution and an external solution. The method comprises the steps of:
 a. introducing a solution of one or more anions selected from phosphate ($PO_4^{3-}$), sulfate ($SO_4^{2-}$) and fluoride ($F^-$) anions into the internal solution;
 b. introducing a solution of cells into the external solution, and capturing the cells within the patch clamp device;
 c. introducing a solution of one or more metal ions selected from $Ca^{2+}$, $Sr^{2+}$ and $Ba^{2+}$, or combinations thereof into the external solution;
wherein the concentration of the $Ca^{2+}$, $Sr^{2+}$ and $Ba^{2+}$ metal ions in the external solution is between 1 and 20 mmol/L.

In a particular case, the method comprises the steps of:
 a. introducing a solution of sulfate ($SO_4^{2-}$) ions into the internal solution;
 b. introducing a solution of cells into the external solution, and capturing the cells within the patch clamp device;
 c. introducing a solution of $Ba^{2+}$ metal ions into the external solution, wherein the concentration of the $Ba^{2+}$ metal ions in the external solution is between 1 and 20 mmol/L.

In this method, steps a and b. can be performed in any order; i.e. a solution of cells can be introduced to the external solution, and captured within the patch clamp device before sulfate solution is introduced in the external solution. However, it is preferred that step a. is performed before step b.

The method may further comprise the step of (d) performing patch clamp measurements on the cell(s) in the patch clamp device.

As for the first aspect, the concentration of anions, in particular sulfate ($SO_4^{2-}$) anions, in the internal solution is between 20 and 200 mmol/L, suitably between 45 and 175 mmol/L, more suitably between 50 and 150 mmol/L, inclusive.

The metal ions are suitably $Ba^{2+}$. The concentration of the metal ions in the external solution is suitably between 4 and 17 mmol/L, more suitably between 5 and 15 mmol/L, inclusive.

Cells for use in the method may be selected from CHO or HEK293.

All details of the first and second aspects, above, are also relevant to this third aspect. In particular, $SO_4^{2-}$ has a relatively high solubility with $Ca^{2+}$. The solubility constant (Ksp) of $CaSO_4$ is $4.93×10^{-5}$. The present technology is useful for applications where $Ca^{2+}$ should have a precise internal concentration over the entire course of the experiment. In the method of the third aspect, therefore, the internal solution and/or the external solution may additionally comprise calcium ($Ca^{2+}$) ions.

Example 1: Test of Ion Pairs as Seal Enhancers in Qube Experiment

Purpose: To test three ion pairs ($BaSO_4$, $SrF_2$, $Ca_3(PO_4)_2$) as seal enhancers on the Qube.

Experimental

Cell line: TE671 expressing the $Na_v1.4$ Channel

Tested ion pairs: $CaF_2$ (reference), $SrF_2$, $BaSO_4$, $Ca_3(PO_4)_2$

Extracted parameters: Cell resistance [MΩ], $Na_v1.4$ current $I_{peak}$ [pA]

Results

The cation in the extracellular (EC) solutions were applied at low concentration (2 mM) during cell addition and positioning and at high concentration (10 mM) before sealing and current measurement.

Priming was carried out at metal ion concentrations of 2 mmol/L. The following cation and anion concentrations were then used:

|  | Extracellular (EC) [mmol/L] | Intracellular (IC) [mmol/L] |
| --- | --- | --- |
| $CaF_2$ (reference seal enhancer) | 10 $Ca^{2+}$ | 140 $F^-$ |
| $SrF_2$ | 10 $Sr^{2+}$ | 140 $F^-$ |
| $BaSO_4$ | 10 $Ba^{2+}$ | 50 $SO_4^{2-}$ |
| $Ca_3(PO_4)_2$ | 10 $Ca^{2+}$ | 50 $PO_4^{3-}$ |

The resulting measured resistance (commonly understood as $R_{membrane}$) and $Na_v1.4$ current ($I_{peak}$) are listed:

|  | $R_{membrane}$ per cell [GΩ] (Mean ± SD) | $I_{peak}$ (nA) per cell (Mean ± SD) |
| --- | --- | --- |
| $CaF_2$ (reference seal enhancer) | 2.3 ± 0.6 | −2.4 ± 0.4 |
| $SrF_2$ | 1.2 ± 0.3 | −2.4 ± 0.5 |
| $BaSO_4$ | 1.1 ± 0.3 | −1.2 ± 0.5 |
| $Ca_3(PO_4)_2$ | 0.4 ± 0.1 | −0.9 ± 0.2 |

Conclusions

Of the three ion pairs tested, the obtained sealing and current levels was best for $SrF_2$, which displayed similar properties as $CaF_2$. The sealing and current levels of the three ion pairs decreased in the order: $SrF_2 > BaSO_4 > Ca_3(PO_4)_2$. It can be seen that sufficient sealing and current levels can be achieved using low concentrations of seal enhancer metal ions.

Example 2: Study of the Effect of the Variation in Metal Ion Concentrations

Based on example one which studied various internal and external solutions in which the concentration of the metal ion in question ($Ca^{2+}$, $Sr^{2+}$ or $Ba^{2+}$) in the external solution was carefully controlled. A further study was conducted in which $BaSO_4$ was characterised as a function of anion and cation concentrations and as an alternative to fluoride based solutions.

The osmolality of the internal solutions is adjusted to 350 mOsm with KCl. The pH of the internal solutions is adjusted to pH 7.0 using KOH.

Test Procedure

Set up: All experiments were carries out on Qube384, automated patch clamp system (—Sophion A/S, Ballerup Denmark) using single hole QChips Cells:
1. CHO cells stably expressing the hERG ion channel
2. HEK293 cells stably expressing the hTMEM16A ion channel General Method:

The internal solutions (at various concentrations of sulfate) are provided to the internal side of the Qube device. A priming solution, containing cells as specified, is then provided to the external side of the Qube device, and cells are captured. The external solutions (at various $Ba^{2+}$ concentrations) are then provided to the external side of the device.

The seal resistance (measured in GΩ) is determined while $Ba^{2+}$ is being provided to the external side, using a voltage pulse train from V=−80 mV to −110 mV for 600 ms.

For each cell type, all four concentrations of sulfate were tested against all four concentrations of barium ion, to provide a 4×4 matrix of results.

TABLE 3

Summary of $R_{membrane}$ from 5 individual experiments (QChips) measured on CHO-hERG cells.

|  |  | $SO_4^{2-}$ | | | |
| --- | --- | --- | --- | --- | --- |
|  |  | 0 mM Mean [GΩ] | 50 mM Mean [GΩ] | 100 mM Mean [GΩ] | 150 mM Mean [GΩ] |
| $Ba^{2+}$ | 0 mM | 0.08 | 0.09 # | 0.04 | 0.01 |
|  | 5 mM | 0.11 ** | 0.71 ### *** | 0.99 ## *** | 0.82 ### *** |
|  | 10 mM | 0.11 | 0.80 ### | 1.70 ### *** | 1.07 ### * |
|  | 15 mM | 0.12 | 1.00 ### *** | 1.84 ### | 1.49 ### *** |

Statistical significance was assessed using an ANOVA test.
* depicts significance with respect to the next lower concentration of Barium and # refers to significance to the next lower sulfate concentration.
* or # indicate p < 0.05;
** or ## indicate p < 0.01;
*** or ### indicate p < 0.001. *

TABLE 4

Summary of $R_{membrane}$ from 1 experiment (QChips) measured on HEK-hTMEM16A cells.

|  |  | $SO_4^{2-}$ | | | |
| --- | --- | --- | --- | --- | --- |
|  |  | 0 mM Mean [GΩ] | 50 mM Mean [GΩ] | 100 mM Mean GΩ] | 150 mM Mean GΩ] |
| $Ba^{2+}$ | 0 mM | 0.03 | 0.20 | 0.11 | 0.03 |
|  | 5 mM | 0.12 | 2.90* | 1.53 | 1.44# |
|  | 10 mM | 0.09 | 2.57 | 4.71 | 0.69### |
|  | 15 mM | 0.1 | 3.62 | 2.86 | 0.58## |

Statistical significance was assessed using an ANOVA test.
*depicts significance with respect to the next lower concentration of Barium and #refers to significance to the next lower sulfate concentration.
*or #indicate p < 0.05;
** or ##indicate p < 0.01;
*** or ###indicate p < 0.001. *

The data provides strong evidence that $BaSO_4$ can be used as seal enhancer in automated patch clamp experiments. This effect seems to be universal as results from different host cell lines that originate from different organisms (Chinese hamster (CHO) and human (HEK293)) showed the same result.

The invention claimed is:

1. A patch clamp system comprising a patch clamp device, an internal solution and an external solution,
   wherein the internal solution comprises one or more anions selected from phosphate ($PO_4^{3-}$) ions, sulfate ($SO_4^{2-}$) ions and fluoride ($F^-$) ions;
   wherein the external solution comprises one or more metal ions selected from $Ca^{2+}$, $Sr^{2+}$, $Ba^{2+}$, or combinations thereof;
   wherein a concentration of the one or more metal ions in the external solution is between 1 and 20 mmol/L;
   wherein the internal solution additionally comprises calcium ($Ca^{2+}$) ions; and
   wherein the internal solution has a concentration of fluoride ($F^-$) ions which is less than 5 mmol/L.

2. The patch clamp system according to claim 1, wherein the concentration of anions in the internal solution is between 20 and 200 mmol/L.

3. The patch clamp system according to claim 1, wherein the metal ions are $Ba^{2+}$ and/or $Sr^{2+}$.

4. The patch clamp system according to claim 1, wherein the anions are sulfate ($SO_4^{2-}$) ions.

5. The patch clamp system according to claim 1, wherein the concentration of the metal ions is between 4 and 17 mmol/L.

6. The patch clamp system according to claim 1, wherein the external solution comprises calcium ($Ca^{2+}$) ions.

7. The patch clamp system according to claim 1, wherein the internal solution has a concentration of fluoride ($F^-$) ions which is zero.

8. A method of making a seal enhancer in a patch clamp system, the method comprising combining one or more anions selected from phosphate ($PO_4^{3-}$), sulfate ($SO_4^{2-}$) and fluoride ($F^-$) anions with one or more metal ions selected from $Ca^{2+}$, $Sr^{2+}$ and $Ba^{2+}$, or combinations thereof, wherein the anions are present in an internal solution, and the metal ions are present in an external solution of the patch clamp system, wherein the concentration of the one or more metal ions in the external solution is between 1 and 20 mmol/L, wherein the internal solution additionally comprises calcium ($Ca^{2+}$) ions, and wherein the internal solution has a concentration of fluoride ($F^-$) ions which is less than 5 mmol/L.

9. A method for providing a gigaseal in a patch clamp system, the patch clamp system comprising a patch clamp device, an internal solution and an external solution, the method comprising the steps of:
   a. introducing a solution of one or more anions selected from phosphate ($PO_4^{3-}$—), sulfate ($SO_4^{2-}$) and fluoride ($F^-$) anions into the internal solution,
      wherein the internal solution additionally comprises calcium ($Ca^{2+}$) ions and wherein the internal solution has a concentration of fluoride ($F^-$) ions which is less than 5 mmol/L;
   b. introducing a solution of cells into the external solution, and capturing the cells within the patch clamp device;
   c. introducing a solution of one or more metal ions selected from $Ca^{2+}$, $Sr^{2+}$, and $Ba^{2+}$, or combinations thereof into the external solution; wherein a concentration of the one or more metal ions in the external solution is between 1 and 20 mmol/L,
   wherein steps a. and b. can be performed in any order.

10. The method according to claim 9, wherein step a. is performed before step b.

11. The method according to claim 9, further comprising performing patch clamp measurements on the cell(s) in the patch clamp device, after step c.

12. The method according to claim 9, wherein the concentration of anions in the internal solution is between 20 and 200 mmol/L.

13. The method according to claim 9, wherein the metal ions are $Ba^{2+}$.

14. The method according to claim 9, wherein the concentration of the metal ions in the external solution is between 4 and 17 mmol/L.

15. The method according to claim 9, further comprising flushing the one or more metal ions from the external solution, after step (c).

16. The method according to claim 9, wherein the cells are selected from CHO or HEK293 cells.

17. A kit for a patch clamp system, the kit comprising an internal solution and an external solution,
   wherein the internal solution comprises one or more anions selected from selected from phosphate ($PO_4^{3-}$—), sulfate ($SO_4^{2-}$) and fluoride ($F^-$) anions;
   wherein the internal solution additionally comprises calcium ($Ca^{2+}$) ions;
   wherein the internal solution has a concentration of fluoride ($F^-$) ions which is less than 5 mmol/L;
   wherein the external solution comprises a solution of one or more metal ions selected from $Ca^{2+}$, $Sr^{2+}$, and $Ba^{2+}$, or combinations thereof; and
   wherein the one or more metal ions are present in the external solution at a concentration between 1 and 20 mmol/L.

18. The kit according to claim 17, wherein the one or more anions are present in the internal solution at a concentration between 20 and 200 mmol/L.

19. The kit according to claim 17, wherein the concentration of the one or more metal ions in the external solution is between 4 and 17 mmol/L.

20. The kit according to claim 17, wherein the concentration of fluoride ($F^-$) ions in the internal solution is zero.

* * * * *